(12) United States Patent
Kajiki et al.

(10) Patent No.: US 7,869,036 B2
(45) Date of Patent: Jan. 11, 2011

(54) ANALYSIS APPARATUS FOR ANALYZING A SPECIMEN BY OBTAINING ELECTROMAGNETIC SPECTRUM INFORMATION

(75) Inventors: Kousuke Kajiki, Tokyo (JP); Toshihiko Ouchi, Sagamihara (JP); Ryota Sekiguchi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 151 days.

(21) Appl. No.: 12/196,224

(22) Filed: Aug. 21, 2008

(65) Prior Publication Data

US 2009/0059226 A1    Mar. 5, 2009

(30) Foreign Application Priority Data

Aug. 31, 2007   (JP)   ............................. 2007-224941
Jun. 27, 2008   (JP)   ............................. 2008-168013

(51) Int. Cl.
*G01J 3/18*   (2006.01)
*G01J 3/20*   (2006.01)
*G01J 3/28*   (2006.01)

(52) U.S. Cl. ................................... 356/328
(58) Field of Classification Search ................. 356/326, 356/328
See application file for complete search history.

(56) References Cited

U.S. PATENT DOCUMENTS

| | | | | |
|---|---|---|---|---|
| 4,687,329 | A * | 8/1987 | Schultz ....................... | 356/328 |
| 7,248,995 | B2 | 7/2007 | Itsuji et al. | |
| 2005/0151966 | A1* | 7/2005 | Packirisamy et al. ........ | 356/328 |
| 2005/0168738 | A1* | 8/2005 | Ohnishi et al. .............. | 356/328 |
| 2006/0085160 | A1 | 4/2006 | Ouchi | |
| 2006/0197021 | A1 | 9/2006 | Ouchi | |
| 2006/0214176 | A1 | 9/2006 | Ouchi et al. | |
| 2006/0227340 | A1 | 10/2006 | Shioda et al. | |
| 2006/0244629 | A1 | 11/2006 | Miyazaki et al. | |
| 2007/0030115 | A1 | 2/2007 | Itsuji et al. | |
| 2007/0195921 | A1 | 8/2007 | Ouchi | |
| 2007/0215808 | A1 | 9/2007 | Sekiguchi et al. | |

(Continued)

FOREIGN PATENT DOCUMENTS

JP          04-363633        * 12/1992

(Continued)

OTHER PUBLICATIONS

U.S. Appl. No. 12/196,084, filed Aug. 21, 2008, Applicant: Ouchi.

(Continued)

*Primary Examiner*—F. L Evans
(74) *Attorney, Agent, or Firm*—Fitzpatrick, Cella, Harper & Scinto (57) ABSTRACT

An analysis apparatus for analyzing a specimen comprises a spectral separator for dispersing spatially an electromagnetic wave introduced from the specimen into spectral components, a sensing element array containing plural sensing elements for sensing the spectral components of the electromagnetic wave dispersed spatially by the spectral separator, and a spectrum calculator for calculating the spectrum from the signal sensed by the sensing elements; the sensing element array having sensitivities different to each of the spectral components of the electromagnetic wave dispersed spatially by the spectral separator, and the spectral separator and the sensing element array being placed so as to receive the spectral components by each of the sensing elements at different incident angles.

10 Claims, 5 Drawing Sheets

U.S. PATENT DOCUMENTS

2007/0229094 A1 10/2007 Kasai et al.
2007/0235718 A1 10/2007 Kasai et al.
2007/0252604 A1 11/2007 Ouchi et al.

FOREIGN PATENT DOCUMENTS

JP     6-26930     2/1994
JP     2005-121574     5/2005

OTHER PUBLICATIONS

U.S. Appl. No. 11/632,958, International Filing Date Aug. 10, 2006, Applicant: Ouchi.

* cited by examiner

ANALYSIS APPARATUS FOR ANALYZING A SPECIMEN BY OBTAINING ELECTROMAGNETIC SPECTRUM INFORMATION

BACKGROUND OF THE INVENTION

1. Field of the Invention

The present invention relates to an electromagnetic analysis apparatus for obtaining electromagnetic spectrum information In particular, the present invention relates to an analysis apparatus for obtaining spectral information of an electromagnetic wave in the frequency range from millimeter-wave band to terahertz band (30 GHz to 30 THz).

2. Description of the Related Art

Techniques are being developed for nondestructive sensing with an electromagnetic wave in the frequency range from a millimeter-wave band to a terahertz band (30 GHz to 30 THz, hereinafter referred to simply as a terahertz (THz) wave). The electromagnetic wave in this frequency range is applied, for example, to safe imaging in place of X-ray fluoroscopic inspection; spectrometric investigation of physical properties by measuring absorption spectrum or complex dielectric constant in the interior of substances; analysis of a biological molecules; evaluation of concentration and mobility of carriers; and so forth.

On the other hand, an analysis apparatus is disclosed which measures optical spectrum by use of an spectroscopic prism and a CCD line image sensor having no mechanical angle-changing mechanism (Japanese Patent Application Laid-Open No. H06-026930 (hereinafter referred to as "Patent Document 1")). With this apparatus, the light to be measured is converted to a parallel light beam by an optical lens system; the light beam is introduced to a spectroscopic prism of fixed deflection; the entire of the spectrum of the light is converted simultaneously into electric signals by a CCD image sensing element, and is corrected by a correction circuit for the wavelength-sensitivity characteristics of the CCD image sensing element; and from the corrected signals, the characteristic spectrum distribution of the light is derived.

Further, a small-sized near-infrared spectral apparatus is disclosed which detects a near-infrared spectrum with a high resolving power, high dynamic range, and high sensitivity (Japanese Patent Application Laid-Open No. 2005-121574 (hereinafter referred to as "Patent Document 2")). The near-infrared spectral apparatus has an input terminal, a diffraction grating, and plural output terminals. The input terminal is placed on the Rowland circle, and the near-infrared light is introduced to the input terminal. The diffraction grating is placed on the Rowland circle and forms spectrum of monochromatic light components. The output terminals are placed on the Rowland circle at the positions where the spectra are focused at nonuniform intervals to decrease the positional deviation of the output terminals from the spectrum-focusing spot.

The present invention is directed to an analysis apparatus for analyzing a specimen, comprising a spectral separator for dispersing spatially an electromagnetic wave introduced from the specimen into spectral components, a sensing element array containing plural sensing elements for sensing the spectral components of the electromagnetic wave dispersed spatially by the spectral separator, and a spectrum calculator for calculating the spectrum from the signal sensed by the sensing elements; the sensing element array having sensitivities different to each of the spectral components of the electromagnetic wave dispersed spatially by the spectral separator, and the spectral separator and the sensing element array being placed so as to receive the spectral components by each of the sensing elements at different incident angles.

The sensing element array can have a constitution for maximizing the sensitivity of sensing of the electromagnetic wave for each of the spectral components dispersed spatially by the spectral separator, the spectral separator and the sensing element array being placed so as to introduce the spectral components to each of the sensing elements at incident angles to maximize the sensitivity of each of the sensing elements.

The electromagnetic wave can cover at least a part of a frequency range from 30 GHz to 30 THz.

The sensing element can have an electromagnetic wave sensor and a filter for selecting the wavelength range for sensing the electromagnetic wave introduced from the specimen; the filter can be constituted of a negative dielectric medium having a negative real part and a second medium; and the negative dielectric medium and the second medium are placed at a distance of not more than the wavelength of the electromagnetic wave to be sensed, and the filter and the electromagnetic wave sensor can be placed at a distance of not more than the wavelength of the electromagnetic wave to be sensed.

The sensing element array can have a plurality of the sensing elements placed on a Rowland circle in accordance with the wavelength dispersion characteristics of the spectral separator.

The apparatus can have a means for compensating deviation of the incident angle or incident position of the electromagnetic wave onto the sensing element.

The sensing element array can receive the electromagnetic wave from a linear region of the specimen; and the spectrum calculator can calculate spectra at plural positions in the linear region.

The apparatus can have a fiber array; the fiber array can receive the electromagnetic wave dispersed spatially into spectral components by the spectral separator and transmits the received electromagnetic wave to the sensing element array; and the electromagnetic wave leaving the fiber array can be introduced to the sensing element to obtain the maximum sensitivity to the sensing element which is designed to give the maximum sensitivity to each of the wavelengths.

In the analysis apparatus, at least one of the spectral separator and the sensing element array can be integrated into a unit, and the unit can be exchangeable.

The apparatus can have a means for projecting the electromagnetic wave onto the specimen.

The present invention is directed to an analysis apparatus for analyzing a specimen, comprising a generator for generating an electromagnetic wave; a diffraction grating for dispersing spatially an electromagnetic wave generated by the generator into spectral components; a sensing element array having a plurality of plasmon type sensing elements for sensing the spectral components of the electromagnetic wave dispersed spatially by the diffraction grating; and a spectrum calculator for calculating the spectra from the intensity of the electromagnetic wave detected by the sensing elements; the sensing element array being constituted to maximize a sensitivity for detecting each of the spectral components of the electromagnetic wave separated spatially by the diffraction grating; and the diffraction grating and the sensing element array being placed so as to introduce the spatially dispersed spectral components to each of the sensing elements at an incident angle to maximize the sensitivity of each of the sensing elements.

However, the method employing the apparatus of the above Patent Documents 1 or 2 tends to give lower sensitivity since no consideration is made on the wavelength dependency of the incident angle for the maximum sensitivity of the sensing element. Therefore, the high-sensitivity and high-speed analysis cannot readily be conducted.

SUMMARY OF THE INVENTION

The analysis apparatus for analyzing a specimen of the present invention comprises a spectral separator, a sensing element array, and a spectrum calculator. The spectral separator separates spatially an electromagnetic wave emitted from a specimen into spectral components. The sensing element array contains plural sensing elements different in sensing sensitivity to electromagnetic waves depending on the wavelength and incident angle of the spectral components of the electromagnetic wave. The spectrum calculator calculates the spectrum of the magnetic wave emitted from the specimen for the signal sensed by the sensing element array. The spectral components of the electromagnetic wave separated spatially by the spectral separator are introduced to the sensing elements having respectively the maximum sensitivity to each of the spectral components.

The present invention enables high-sensitivity analysis of a specimen by introducing the spectral components of the electromagnetic wave separated spatially to the sensing elements so as to obtain maximum sensitivities at each of the wavelengths.

Further features of the present invention will become apparent from the following description of exemplary embodiments with reference to the attached drawings.

DESCRIPTION OF THE EMBODIMENTS

The apparatus for analysis of a specimen of the present invention is described with reference to drawings.

Figure 1:
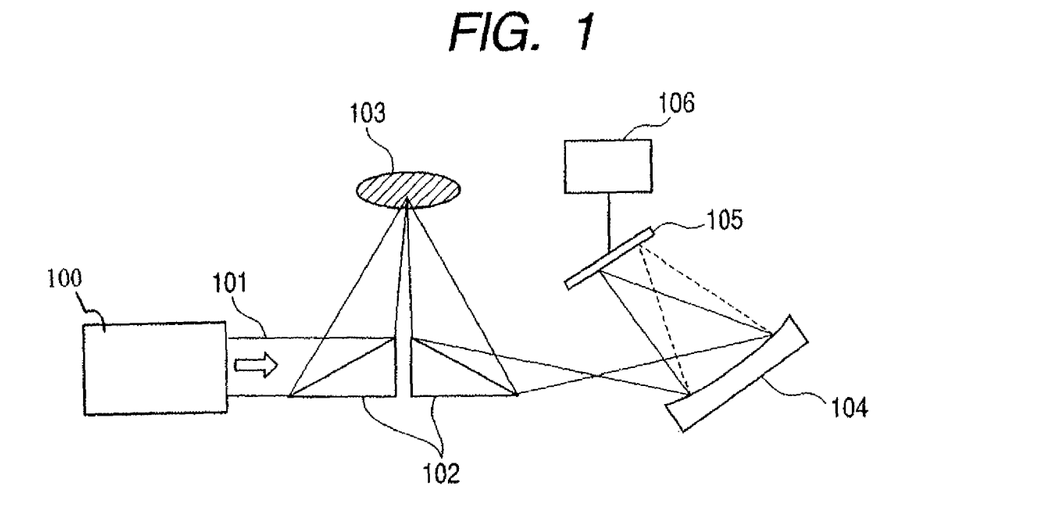
FIG. 1 illustrates a constitution of an embodiment of the analysis apparatus of the present invention.

FIG. 1 illustrates a constitution of an embodiment of the analysis apparatus of the present invention. In FIG. 1, optical system 102 on the specimen side projects electromagnetic wave 101 onto specimen 103, receives the electromagnetic wave reflected by specimen 103, and transmits the electromagnetic wave to diffraction grating 104. Diffraction grating 104 serves as the spectral separator for separating spatially the electromagnetic wave from the specimen into spectral components.

Sensing element array 105 contains plural sensing elements for sensing the spectral components dispersed spatially by diffraction grating 104. For instance, sensing element array 105 has a structure illustrated in FIG. 2, and the sensitivity in sensing of the electromagnetic wave varies for each of the spectral components dispersed spatially by the spectral separator (diffraction grating) 104. The plural sensing elements 201 are preferably constituted to have the maximum sensitivity for each of the spectral components dispersed spatially by the spectral separator (diffraction grating) 104.

Figure 2:
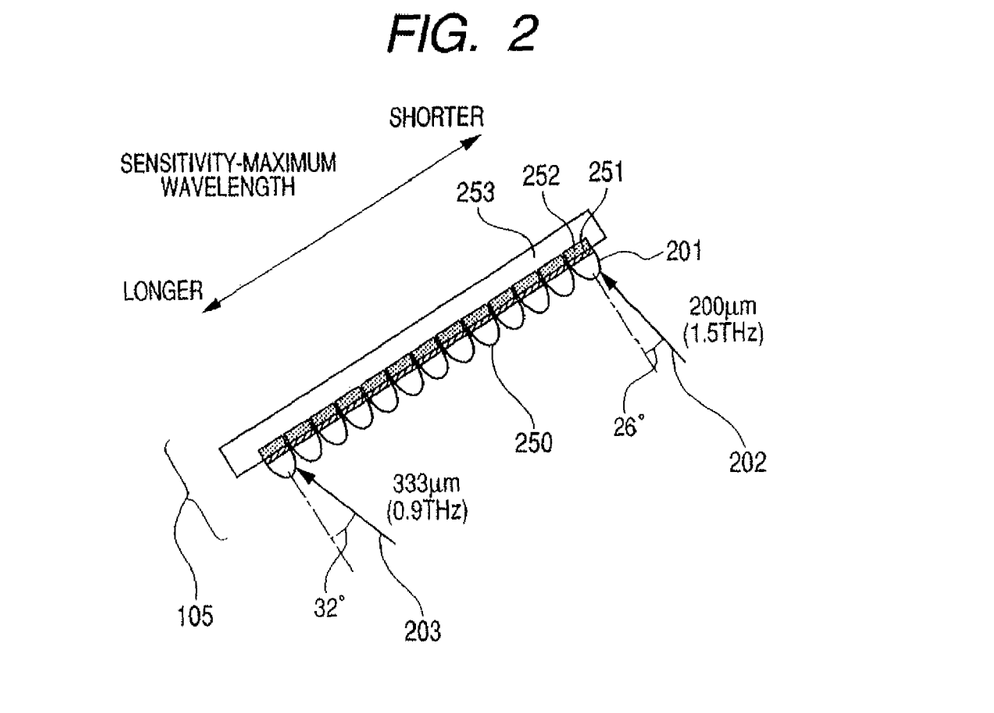
FIG. 2 illustrates a sensing element array employed in the present invention.

The spectral separator (diffraction grating) 104 and the sensing element array are placed so that the incident angles, to sensor elements 201, of the spectral components dispersed spatially by the spectral separator are different for each of the sensing elements. The spectral separator and the sensing element array are preferably placed so that the sensitivity of each of the sensing elements 201 becomes maximum. The sensing element array 105 contains plural sensing elements 201 which have electromagnetic wave-sensing sensitivity depending on the wavelength and incident angle of electromagnetic wave. Incidentally, the sensitivity may be evaluated by an output current from sensing element 201 for a unit input power of the electromagnetic wave.

The optical system 102 at the specimen side may be constituted of conventional optical elements. In FIG. 1, electromagnetic wave 101 is reflected by specimen 103. However, in another constitution, the electromagnetic wave may be allowed to penetrate specimen 103. The irradiation spot of electromagnetic wave 101 on specimen 103 and the placement of specimen 103 may relatively be shifted to obtain the spectrum at plural spots on specimen 103. Fibers may be employed for transmission and irradiation of electromagnetic wave 101 close to specimen 103 and receiving the electromagnetic wave therefrom. Otherwise, electromagnetic waves in near-field region may be sensed by sensing element array 105.

Spectral separator (diffraction grating) 104 is not limited, insofar as the wavelength of electromagnetic wave 101 can be spatially dispersed and can be introduced to sensing element array 105. Spectral separator includes a prism or a photonic crystal.

Sensing elements 201 are arranged in the order of the wavelengths for maximum sensitivities. Diffraction grating 104 and sensing element array 105 are constituted so that the spectral components of the electromagnetic wave are introduced respectively to correspond nearly to the incident angles for the maximum sensitivities. The incident angle of the spectral components need not correspond precisely to the sensitivity maximum, but may deviate from the sensitivity maximum.

The signals of electromagnetic wave 101 sensed by sensing element array 105 are transmitted to spectrum calculator 106. This calculator calculates the spectra of the electromagnetic wave 101 from the intensity signals of the electromagnetic wave sensed by the sensing elements. In spectrum calculator 106, the electromagnetic wave intensities obtained by each of the elements of sensing element array 105 are allowed to correspond with the wavelengths. Spectrum calculator 106 may have a means for correcting the diffraction efficiency of diffraction grating 104. From the characteristics of the spectrum distribution derived by spectrum calculator 106, information can be obtained on properties of specimen 103.

Sensing element array 105 is constituted to obtain a higher sensitivity to each of the spectral components dispersed spatially by the spectral separator. Further, the incident angles of the spatially dispersed electromagnetic wave components are selected to increase the sensitivity of each of the sensing element 201. The sensitivity is preferably made maximum. For example, when sensing element 201 utilizes a surface plasmon, the sensitivity becomes the maximum at the resonance angle. This is described below in detail with reference to drawings. Further, relative constitution of the diffraction grating (spectral separator) and the surface plasmon (sensing element) is described below with reference to drawings.

(Generator 100)

The electromagnetic wave may contain various spectral components. The electromagnetic wave may be generated by a single light source, or may be synthesized from electromagnetic waves generated by plural light sources. The source (generator 100) of electromagnetic wave 101 may be a quantum cascade laser, or a resonance tunnel diodes or Gunn diodes combined with a higher harmonic wave generator. When the generator is large in size, a backward wave oscillator or a parametric generator employing a nonlinear crystal element is useful. Otherwise, the electromagnetic wave may be generated by irradiation of femto-second laser onto a photoconductive element. Electromagnetic wave 101 may be pulsed or continuous. The wavelength may be changed with time. With the temporally changed wavelength, different wavelengths of light beams are introduced successively to diffraction gratings 104, whereby electromagnetic wave 101 is allowed to scan spatially sensing element array 105. Specimen-side optical system 102 may be a parabolic mirror or a lens. The electromagnetic wave 101 may be focused on specimen 103, or may be allowed to spread spatially like a parallel light beam, or may be introduced to diffraction grating 104 as a reflected light beam or a transmitted light beam. The apparatus illustrated in FIG. 1 has a means for projecting electromagnetic wave 101 to specimen 103. In contrast, the apparatus may be of a passive sensing system which does not project an electromagnetic wave to specimen 103 but only receives a light beam. With a system of projecting electromagnetic wave 101 to specimen 103, the intensity of the signal from sensing element array 105 can be increased by increasing the quantity of the light introduced to sensing element array 105.

(Surface Plasmon)

Sensing element 201 may have a filter for selecting the wavelength range of sensing of the electromagnetic wave transmitted from specimen 103, and an electromagnetic wave sensor like that illustrated in FIG. 2. The filter is constituted of a negative dielectric medium 251 having a negative real part of the dielectric constant and a second medium 250. The negative dielectric medium 251 and the second medium 250 are placed at a distance not longer than the wavelength of the electromagnetic wave to be detected. Further, the filter assembly 250, 251 and electromagnetic wave sensor 252 are placed at a distance not longer than the wavelength of the electromagnetic wave to be sensed. In this sensing element, the incident light is converted to surface plasmon at the interface between negative dielectric medium 251 and electromagnetic wave sensor 252. The surface plasmon has a high electric field intensity, localizing at the interface. Electromagnetic wave sensor 252 is placed in this high electric field intensity, enabling high-sensitivity sensing. In FIG. 2, the numeral 253 denotes the substrate for sensing element array 105.

Figure 3:
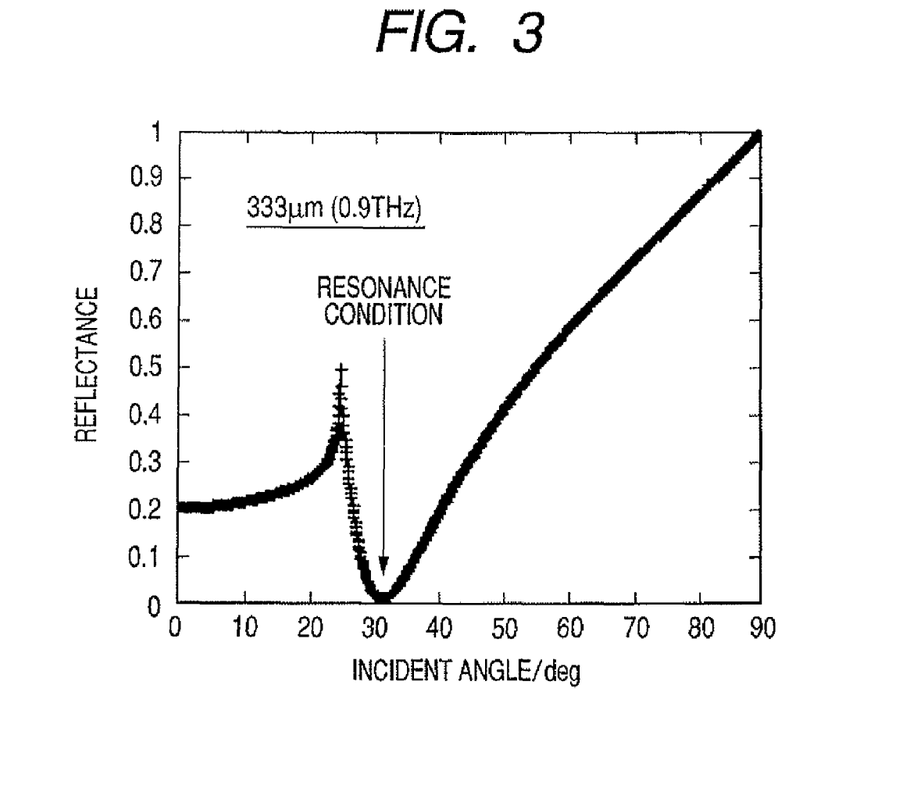
FIG. 3 illustrates an example of dependence of the reflectance on the incident angle in a plasmon sensing element.
Figure 4:
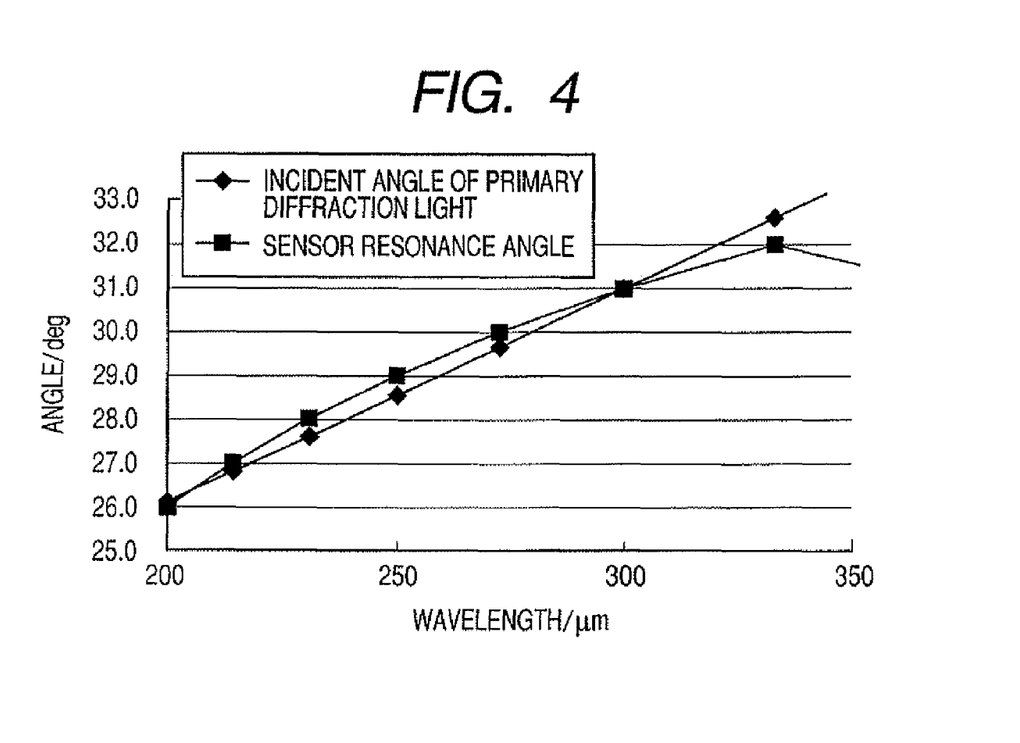
FIG. 4 illustrates an example of dependence, on the wavelength, of the incident angle of the primary diffraction light introduced to the sensing element array and of the resonance angle of the sensing element.

The sensing element described above as an example is called, hereinafter for convenience, a plasmon type sensing element. The sensitivity of plasmon type sensing element 201 is described with reference to FIG. 3. In FIG. 3, the abscissa denotes the incident angle of the electromagnetic wave onto the plasmon type sensing element 201, and the ordinate denotes the reflectance. FIG. 3 is a graph illustrating an example of an electromagnetic wave having a wavelength of 333 μm (0.9 THz). As shown in FIG. 3, under the conditions of the resonance angle, the incident light introduced to the plasmon type of sensing element 201 is nearly entirely converted to surface plasmon in the interior of sensing element 201 to result in the minimum reflectance. The lower reflectance gives the higher the sensitivity of the plasmon type sensing element 201, since the plasmon type sensing element senses mainly the electric field strength of the surface plasmon. Therefore, the sensitivity becomes the maximum at the resonance angle in FIG. 3. The half width of the angle is, for example, 10 degrees.

The resonance angle depends on the wavelength. The dependence of the incident angle for the maximum sensitivity is estimated in the wavelength range from 200 μm to 333 μm based on such a drawing. In an example, the incident angle for the maximum sensitivity is found to distribute in the range from 26 degrees to 32 degrees. For example, as illustrated in FIG. 2, primary diffraction light beam 202 corresponding to a wavelength 200 μm is introduced to one end of the plasmon type sensing element array 105, and primary diffraction light beam 203 corresponding to a wavelength 300 μm is introduced to the other ends thereof. Between the both ends, plural plasmon type sensing elements 201 having respectively a sensitivity maximum in the range from 200 μm to 333 μm are placed in the order of the sensitivity-maximum wavelengths.

(Arrangement of Diffraction Grating and Surface Plasmon)

An arrangement of diffraction grating 104 and sensing element array 105 is described below. As described above, each of the elements of sensing element array 105 has a maximum sensitivity at different wavelengths. The arrangement is designed to introduce the electromagnetic wave corresponding approximately to the maximum-sensitivity wavelength to each of the sensing elements.

Figure 10:
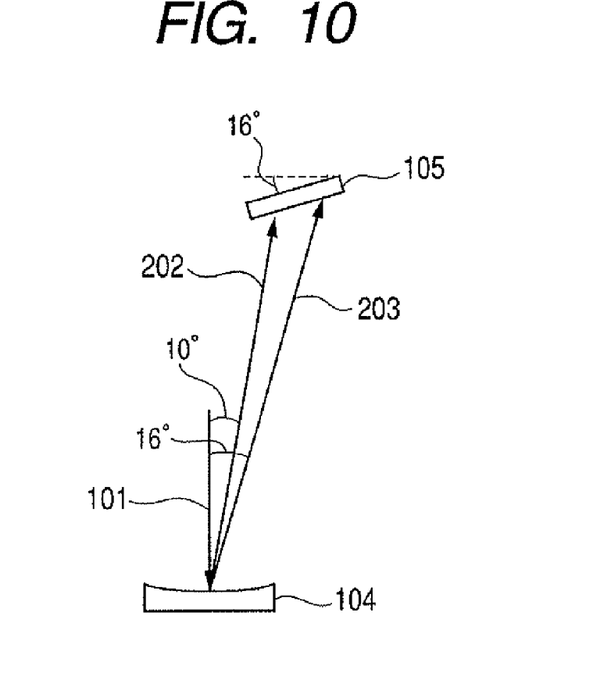
FIG. 10 illustrates a relative angle between the diffraction grating and the sensing element array.

Diffraction grating 104 for introducing electromagnetic wave 101 to plasmon type sensing element array 105 is designed so as to meet the relation between the aforementioned wavelength and the incident angle for the maximum sensitivity in plasmon type sensing elements 201. In this embodiment, to simplify the description, a concave diffraction grating is used which has a spectroscope function and a focusing function combinedly. However, a different type of diffraction grating may be employed. Here, an example of relative angle between diffraction grating 104 and sensing element array 105 is described with reference to FIG. 10. In perpendicular introduction of electromagnetic wave 101 to diffraction grating 104, the pitch of the grooves of diffraction grating 104 is made to be 1200 μm, and the relative angle between diffraction grating 104 and sensing element array 105 is changed from parallel by 16 degrees. Thereby, for electromagnetic waves in the range from 200 μm to 333 μm, the incident angle of the primary diffraction light and the resonance angle of plasmon type sensing elements 201 can be made approximately equal.

In this constitution, the spectral resolution depends on the element pitch in plasmon type sensing element array 105, and the distance between diffraction grating 104 and element array 105. In an example, the distance between diffraction grating 104 and plasmon type sensing element array 105 is 500 mm, and the pitch of plasmon type sensing element array is 6.85 mm. In this constitution, the wavelength resolution is one tenth of the wavelength difference between 200 μm and 333 μm, namely about 13.3 μm. With the element pitch of 0.685 mm in plasmon type sensing element array 105, the wavelength resolution is about 1.33 μm. In another method of improving the wavelength resolving power, the focal length of diffraction grating 104 may be increased and the distance between the diffraction grating 104 and plasmon type sensing element array 105 may be increased. Otherwise, the pitch in the diffraction grating 104 may be changed for the wavelength dispersion property.

In the above description, a primary diffracted light is utilized, but a higher order of the diffracted light may naturally be utilized to meet the purpose.

As described above, according to the present invention, the incident angle of the electromagnetic wave can be matched for each of the sensing elements to improve the sensitivity of the sensing element sensitivity for high sensitivity analysis, and higher analysis speed. For nondestructive sensing of the specimen, the electromagnetic wave is a terahertz wave including at least a part of the wavelength region from 30 GHz to 30 THz.

EXAMPLES

Example 1

Concave Diffraction Grating

Figure 5:
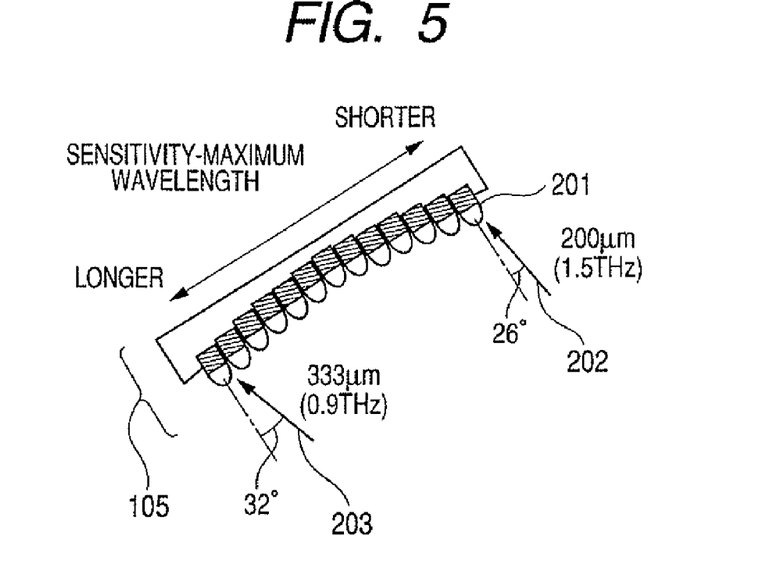
FIG. 5 illustrates a sensing element array in Example 1.

In the analysis apparatus of this Example, sensing elements are arranged in the sensing element array to meet the wavelength dispersion property of the wavelength dispersion element as the spectral separator. FIG. 5 illustrates a sensing element array of this Example. The other portions of the analysis apparatus are similar to those described above.

In FIG. 5, sensing elements 201 of sensing element array 105 are placed on a circle circumference, not on a line. This circle is a Rowland circle of the concave diffraction grating. The Rowland circle is a circle having a radius of a half the curvature of the concave diffraction grating, and placed so as to be tangent to the center of the concave diffraction grating. For example, the radius of the Rowland circle can be made to be 500 mm for the curvature radius 1000 mm of the concave diffraction grating. A beam of the electromagnetic wave emitted from one point on the Rowland circle is diffracted by the concave grating, and the diffracted light beams are focused respectively on one point on the Rowland circle. Therefore, sensing elements 201 placed on the Rowland circle as in this Example are capable of receiving respectively the diffracted light more effectively than those placed on a line to improve the wavelength resolving power.

In arrangement of the elements in sensing element array 105, the inclination directions of each of the elements may be adjusted to introduce the electromagnetic wave to each of the elements at a maximum sensitivity. Otherwise, the elements are placed at non-uniform intervals to introduce the electromagnetic wave at a maximum sensitivity to each of the elements. As described above, the sensing element array contains the sensing elements placed on a non-linear line or in a non-uniform intervals in accordance with the wavelength separation characteristics to introduce wave to each of the elements at the maximum sensitivity.

In the above description, the element arrangement in sensing element array 105 is designed. Otherwise, spatial wavelength dispersion of the wavelength element or annexed optical element may be designed, or the faces of the sensing elements may be inclined from the array face to introduce the electromagnetic wave to each of the element at an incident angle for the maximum sensitivity.

Example 2

Control of Incident Angle to Sensing Element

Figure 6:
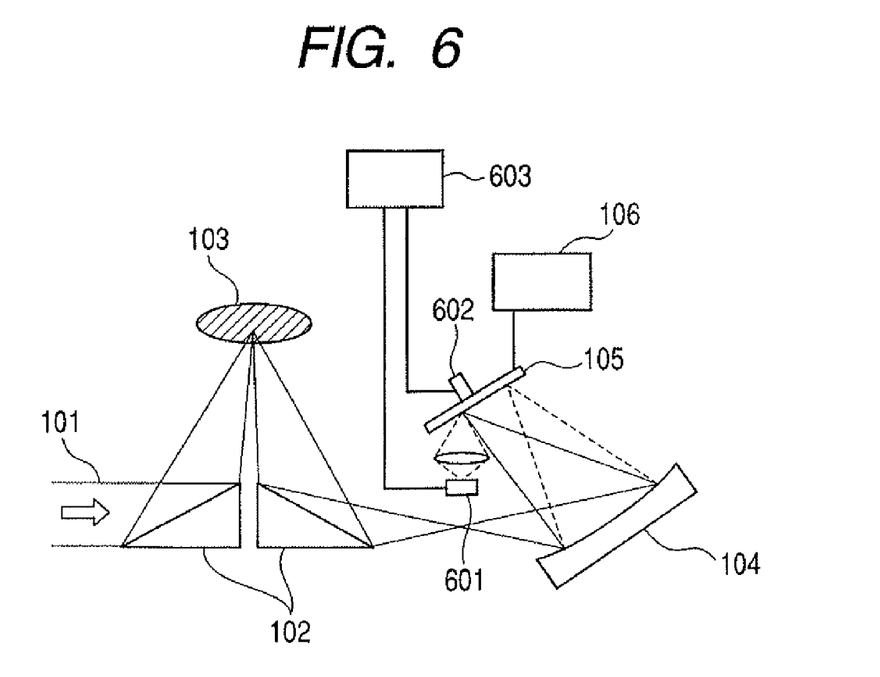
FIG. 6 illustrates an analysis apparatus employed in Example 2.

The analysis apparatus of this Example has a mechanism for compensating a variation of the incident angle or incident position of the electromagnetic wave introduced from the specimen. FIG. 6 illustrates an analysis apparatus of this Example.

The operation of the analysis apparatus in this Example is described below. Reflected light detector 601 receives a light beam reflected by a sensing element having the maximum sensitivity at the wavelength of 333 μm from among the elements in sensing element array 105. The information on the reflected light intensity is transmitted to inclination controller 603. The inclination controller controls the inclination of the sensing element array 105 by inclination control mechanism 602 with a motor or a like device in accordance with the information. For example, the inclination is controlled to keep nearly minimum the reflected light intensity. This corresponds to the control of the incident angle of the electromagnetic wave to sensing element 201 to be approximately the resonance angle, as understood from FIG. 3. The control can be conducted by a conventional peak-lock method, in which the inclination of sensing element array 105 is kept swing in a narrow range and from the rate of the change of the reflected light intensity, the direction of the minimum intensity of the reflected light is detected to control the inclination of the sensing element array 105.

Otherwise, a control mechanism employing a piezo element may be used in place of the above control mechanism. With this piezo system, a high-speed control can be realized.

With the above constitution, even when the position or incident angle of the electromagnetic wave introduced from specimen 103 to specimen-side optical system 102 deviates, the sensing element array 105 can be inclined to compensate the deviation. Thereby the analysis can be conducted without an influence of the variation of the position or angle of specimen 103.

In this Example, the intensity of the light reflected by sensing element 201 corresponding to an electromagnetic wave of 333 μm is measured. However, the intensity of the light reflected by other element or elements may be measured. Further, in place of the control of the inclination of sensing element array 105, inclination of diffraction grating 104 or of other optical element may be controlled. Other than the inclination, for example, the center position of the sensing element array 105 may controlled.

Example 3

Linear Region of Specimen

Figure 7:
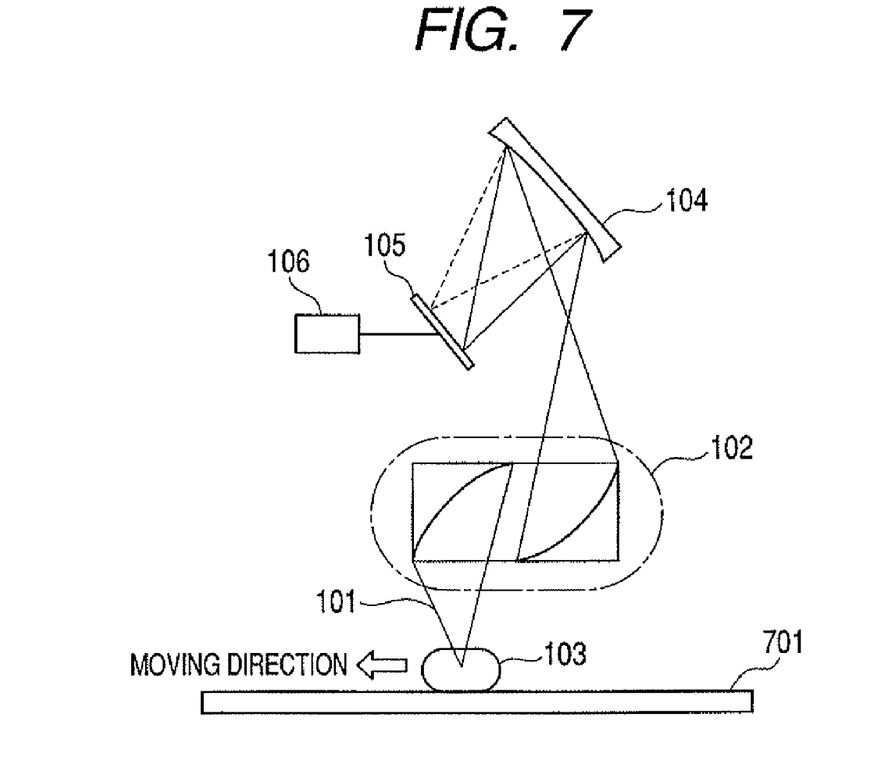
FIG. 7 illustrates an analysis apparatus employed in Example 3.

The analysis apparatus of this Example calculates spectra at plural positions in a linear region from an electromagnetic wave derived from the linear region of a specimen. FIG. 7 illustrates the analysis apparatus of this Example.

Figure 8A:
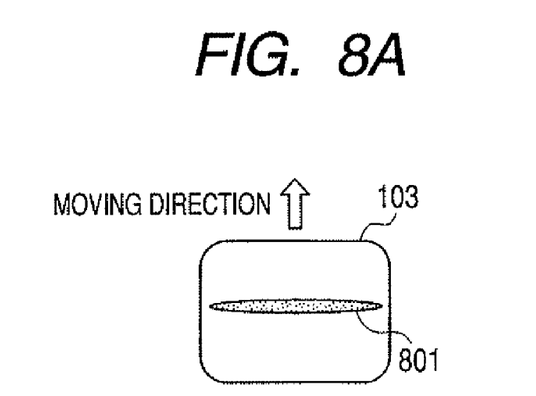
FIGS. 8A and 8B illustrate a linear sensing region (a) of a specimen, and a sensing element array (b) in Example 3.
Figure 8B:
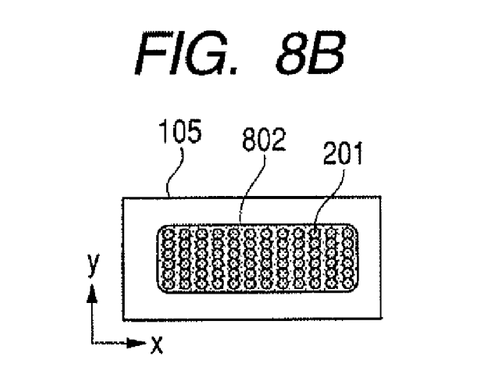

In FIG. 7, the numeral 103 denotes a specimen, and the numeral 102 denotes a specimen-side optical system. The apparatus of the Example, as illustrated in FIG. 8A, is constituted such that electromagnetic wave 101 derived from linear sensing region 801 of specimen 103 is received by sensing element array 105. Electromagnetic wave 101 forms a real image at an intermediate point between specimen-side optical system 102 and concave diffraction grating 104. The real image is preferably formed on the Rowland circle of concave diffraction grating 104. With such a constitution, the electromagnetic wave is dispersed and is introduced onto sensing elements 802 of sensing element array 105 as illustrated in FIG. 8B at positions in the x-direction with a wavelength represented in the y-direction. Thus, the spectra of portions of linear sensing region 801 of specimen 103 are derived.

Since the concave diffraction grating generally causes remarkable astigmatism, the focus points deviate considerably in the x-direction and y-direction in FIGS. 8A and 8B. The position-resolving power and the wavelength-resolving power can be improved by making the concave diffraction grating 104 aspherical.

The spectra throughout the entire specimen 103 can be derived by moving the linear region 801 of specimen 103 stepwise by belt conveyor 701 in the "movement direction" shown in FIG. 7.

Example 4

Fiber

Figure 9:
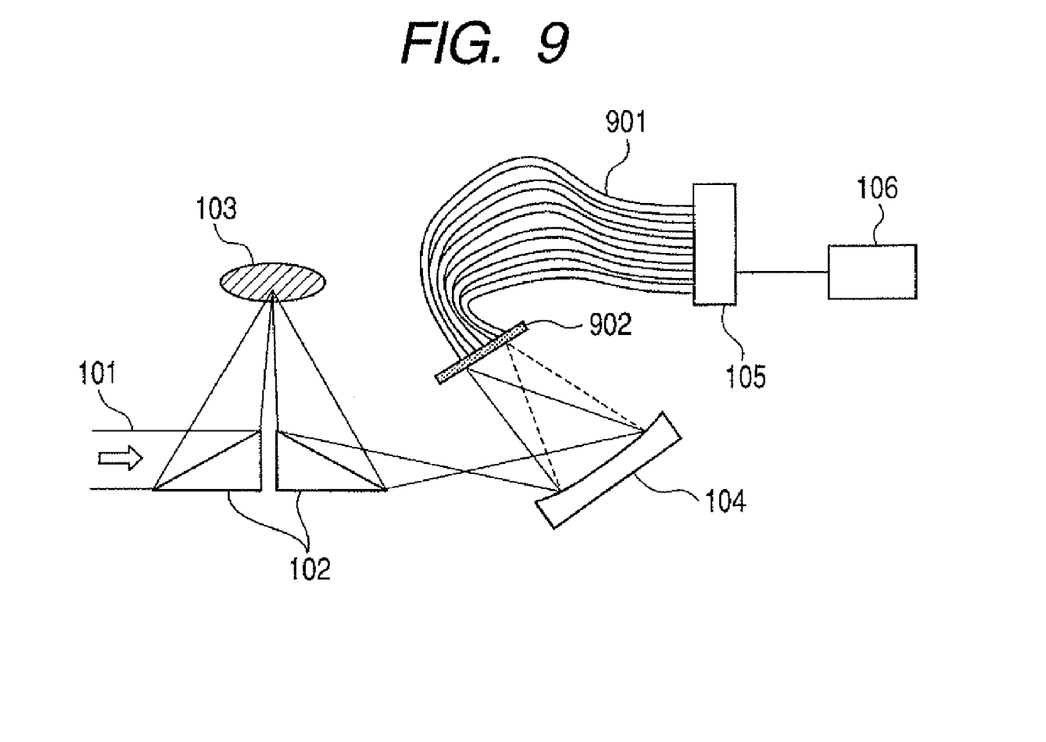
FIG. 9 illustrates an analysis apparatus employed in Example 4.

In the analysis apparatus of this Example, an electromagnetic wave emitted from a spectral separator is received by a fiber and is transmitted to a sensing element array. FIG. 9 illustrates the analysis apparatus of this Example.

In FIG. 9, electromagnetic wave 101 dispersed spatially by diffraction grating 104 is transmitted through light-receiver 902 to the fibers 901. At the ends of the fibers, a micro-lens may be attached, for example, to improve the coupling efficiency of the electromagnetic wave. The received electromagnetic wave is transmitted through the fibers 901 to sensing element array 105. The transmission line suitable in the terahertz bands includes hollow fibers and surface waveguides. Fibers 901 and sensing element array 105 are coupled to meet the incident angle at the maximum sensitivity wavelength of each of the elements of sensing element array 105. In such a manner, the electromagnetic wave from the sensing element array is introduced to the sensing elements constituted so as to achieve the maximum sensitivity to each of the wavelengths.

With such a constitution, the incident angle of the electromagnetic wave can be matched readily with sensing element array 105. Further, the fiber ends can readily be placed at the focusing points of the diffracted light, which enables improvement of the wavelength resolution.

Example 5

Switching of Plural Units

In this Example, the sensing element array and the diffraction grating are integrated into a unit. The analysis apparatus of this Example has this unit in plurality, and the units can be switched to meet the purpose of the analysis, such as change of the resolving power. As the unit, sensing element array 105 and diffraction grating 104 are fixed in a package to keep the relative position unchanged. Such a unit is provided in plurality, and can be switched on the optical path from specimen-side optical system 102. The plural units are different, for example, in resolving power. The resolving power can be made different, for example, by adjusting the grating pitch of diffraction grating 104, or the distance between diffraction grating 104 and sensing element array 105. The units in plurality enables to meet the preference of the analysis such as resolving power, and spectral estimation speed. As described above, in the Example, the spectral separators and the sensing elements are combined in pairs as units, and the units can be exchanged.

The unit may contain the entire or a part of the specimen-side optical system 102. For example, the focusing distances in the units are changed to meet different type of specimens 103. Otherwise, light receiver 902 of the fibers and diffraction grating 104 mentioned in Example 4 may be unitized.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2007-224941, filed Aug. 31, 2007 and No. 2008-168013, filed Jun. 27, 2008 which are hereby incorporated by reference herein in their entirety.

What is claimed is:

1. An analysis apparatus for analyzing a specimen, comprising:

a spectral separator for dispersing spatially an electromagnetic wave from the specimen into spectral components;

a sensing element array containing plural sensing elements for sensing the spectral components of the electromagnetic wave dispersed spatially by the spectral separator; and a spectrum calculator for calculating a spectrum based on a signal from the sensing elements;

wherein the spectral separator and the sensing element array are placed so that the incident angles of the spectral components dispersed spatially by the spectral separator to the sensor elements are different for each of the sensing elements, wherein the sensing element has an electromagnetic wave sensor and a filter for selecting the wavelength range for sensing the electromagnetic wave introduced from the specimen, wherein the filter comprises a negative dielectric medium having a negative real part and a second medium, wherein the negative dielectric medium and the second medium are placed at a distance of not more than the wavelength of the electromagnetic wave to be sensed, and wherein the filter and the electromagnetic wave sensor are placed at a distance of not more than the wavelength of the electromagnetic wave to be sensed.

2. The analysis apparatus according to claim 1, wherein the spectral separator and the sensing element array are placed so as to introduce the spectral components to each of the sensing elements at incident angles to maximize the sensitivity of each of the sensing elements.

3. The analysis apparatus according to claim 1, wherein the electromagnetic wave covers at least a part of a frequency range from 30 GHz to 30 THz.

4. The analysis apparatus according to claim 1, wherein the sensing element array has a plurality of the sensing element placed on a Rowland circle in accordance with the wavelength dispersion characteristics of the spectral separator.

5. The analysis apparatus according to claim 1, wherein the apparatus has a means for compensating deviation of the incident angle or incident position of the electromagnetic wave onto the sensing element.

6. The analysis apparatus according to claim 1, wherein the sensing element array receives the electromagnetic wave from a linear region of the specimen; and the spectrum calculator calculates spectra at plural positions in the linear region.

7. The analysis apparatus according to claim 1, wherein the apparatus has a fiber array;

the fiber array receives the electromagnetic wave dispersed spatially into spectral components by the spectral separator and transmits the received electromagnetic wave to the sensing element array; and the electromagnetic wave leaving the fiber array is introduced to the sensing element to obtain the maximum sensitivity to the sensing element which is designed to give the maximum sensitivity to each of the wavelengths.

8. The analysis apparatus according to claim 1, wherein at least one of the spectral separator and the sensing element array are integrated into a unit, and the unit is exchangeable.

9. The analysis apparatus according to claim 1, wherein the apparatus has a means for projecting the electromagnetic wave onto the specimen.

10. An analysis apparatus for analyzing a specimen, comprising:

a generator for generating an electromagnetic wave;

a diffraction grating for dispersing spatially an electromagnetic wave from the generator into spectral components;

a sensing element array having a plurality of plasmon type sensing elements for sensing the spectral components of the electromagnetic wave dispersed spatially by the diffraction grating; and a spectrum calculator for calculating a spectrum based on a signal from the sensing elements, wherein each of the sensing elements is configured to maximize a sensitivity for detecting each of the spectral components of the electromagnetic wave separated spatially by the diffraction grating, and wherein the diffraction grating and the sensing element array are placed so as to receive the spatially dispersed spectral components by the sensing elements at incident angles to maximize the sensitivities of each of the sensing elements.

* * * * *